(12) United States Patent
Kanae

(10) Patent No.: US 10,668,245 B2
(45) Date of Patent: Jun. 2, 2020

(54) CATHETER AND MANUFACTURING METHOD OF CATHETER

(71) Applicant: TERUMO KABUSHIKI KAISHA, Shibuya-ku, Tokyo (JP)

(72) Inventor: Tsuyoshi Kanae, Shizuoka (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 30 days.

(21) Appl. No.: 15/703,276

(22) Filed: Sep. 13, 2017

(65) Prior Publication Data

US 2018/0015249 A1 Jan. 18, 2018

Related U.S. Application Data

(63) Continuation of application No. PCT/JP2016/058261, filed on Mar. 16, 2016.

(30) Foreign Application Priority Data

Mar. 20, 2015 (JP) .................................. 2015-058537

(51) Int. Cl.
*A61M 25/00* (2006.01)
*A61M 25/10* (2013.01)
(Continued)

(52) U.S. Cl.
CPC .... *A61M 25/0009* (2013.01); *A61M 25/0015* (2013.01); *A61M 25/1036* (2013.01);
(Continued)

(58) Field of Classification Search
CPC .......... A61M 25/0169; A61M 25/0029; A61M 25/0052; A61M 25/104; A61M 25/10;
(Continued)

(56) References Cited

U.S. PATENT DOCUMENTS 3,805,794 A * 4/1974 Schlesinger ...... A61M 25/0069
604/534
4,610,660 A * 9/1986 Rosenberg ........ A61M 25/1025
604/102.02
(Continued)

FOREIGN PATENT DOCUMENTS

EP 1 676 594 B1 9/2008
JP 2004-503304 A 2/2004
(Continued)

OTHER PUBLICATIONS

English translation of Written Opinion of the International Searching Authority dated Jun. 7, 2016, in corresponding International Application No. PCT/JP2016/058261.
(Continued)

*Primary Examiner* — Laura A Bouchelle
*Assistant Examiner* — Mark A Igel
(74) *Attorney, Agent, or Firm* — Buchanan Ingersoll & Rooney PC

(57) ABSTRACT

A catheter and a manufacturing method thereof are disclosed, which can restrain a guide wire lumen and a dilation lumen from communicating with each other during thermal fusion-bonding while suppressing an increase in an outer diameter of a catheter shaft. A catheter has a catheter shaft in which a distal side shaft, an inner tube shaft, and a proximal side shaft are integrated with each other in a fusion region. The inner tube shaft has an opening portion which, opens outward and an arc-shaped portion which extends from the opening portion to a proximal side and which has only a portion of an entire circumference in a circumferential direction of the inner tube shaft. The fusion region includes the opening portion located on a distal side of a proximal end of the distal side shaft.

17 Claims, 13 Drawing Sheets

(51) Int. Cl.
*A61M 25/01* (2006.01)
*B29C 63/00* (2006.01)
*B29C 63/18* (2006.01)
*B29L 31/00* (2006.01)

(52) U.S. Cl.
CPC .......... B29C 63/00 (2013.01); B29C 63/0069 (2013.01); B29C 63/18 (2013.01); *A61M 25/0032* (2013.01); *A61M 25/0052* (2013.01); *A61M 25/01* (2013.01); *A61M 2025/0004* (2013.01); *A61M 2025/0183* (2013.01); *B29L 2031/7543* (2013.01)

(58) Field of Classification Search
CPC .............. A61M 25/00; A61M 25/1006; A61M 25/0043; A61M 2025/0183; A61M 2025/0177; A61M 2025/018; A61F 2/958
USPC ........................................................ 604/921
See application file for complete search history.

(56) References Cited

U.S. PATENT DOCUMENTS

| | | | | | |
|---|---|---|---|---|---|
| 4,748,982 | A * | 6/1988 | Horzewski | ........ | A61M 25/0054 604/102.02 |
| 4,944,745 | A * | 7/1990 | Sogard | ................ | A61M 25/104 604/103 |
| 5,156,594 | A * | 10/1992 | Keith | ................ | A61M 25/0662 604/103.09 |
| 5,209,729 | A * | 5/1993 | Hofmann | ............ | A61M 25/104 604/102.02 |
| 5,279,562 | A * | 1/1994 | Sirhan | ................ | A61M 25/104 604/103.09 |
| 5,306,247 | A * | 4/1994 | Pfenninger | ........... | A61M 29/02 604/102.02 |
| 5,330,499 | A * | 7/1994 | Kanesaka | ......... | A61M 25/1025 604/921 |
| 5,368,567 | A * | 11/1994 | Lee | ..................... | A61M 25/104 604/103.1 |
| 5,387,193 | A * | 2/1995 | Miraki | ................ | A61M 25/104 604/102.02 |
| 5,533,968 | A * | 7/1996 | Muni | .................... | A61L 29/041 604/103.11 |
| 6,409,863 | B1 * | 6/2002 | Williams | .......... | A61M 25/0009 156/198 |
| 2001/0056285 | A1 * | 12/2001 | Dutta | .................. | A61M 25/104 606/194 |
| 2006/0064074 | A1 * | 3/2006 | Mallaby | ................ | A61M 25/10 604/523 |
| 2006/0142696 | A1 * | 6/2006 | Kumoyama | ...... | A61M 25/0023 604/103.04 |
| 2007/0151650 | A1 * | 7/2007 | Simpson | ........... | A61M 25/0023 156/1 |
| 2008/0045928 | A1 * | 2/2008 | Simpson | ........... | A61M 25/1036 604/525 |
| 2010/0217234 | A1 * | 8/2010 | Grovender | .............. | A61L 29/06 604/523 |
| 2011/0137245 | A1 * | 6/2011 | Schaeffer | ................ | A61L 29/04 604/103.02 |
| 2012/0271232 | A1 * | 10/2012 | Katsurada | ......... | A61M 25/0052 604/103.09 |
| 2012/0296367 | A1 * | 11/2012 | Grovender | ........ | A61M 25/0012 606/192 |
| 2012/0302952 | A1 * | 11/2012 | Kitada | .............. | A61M 25/0021 604/96.01 |
| 2013/0116618 | A1 * | 5/2013 | Chouinard | ........ | A61M 25/0029 604/96.01 |
| 2016/0067458 | A1 * | 3/2016 | Torres | ..................... | A61L 29/06 604/96.01 |

FOREIGN PATENT DOCUMENTS

| | | |
|---|---|---|
| JP | 2006-187315 A | 7/2006 |
| JP | 2012-228296 A | 11/2012 |
| JP | A-2014-195487 | 10/2014 |
| WO | WO 01/95973 A2 | 12/2001 |
| WO | 2012/042619 A2 | 4/2012 |

OTHER PUBLICATIONS

International Search Report (PCT/ISA/210) dated Jun. 7, 2016, by the Japanese Patent Office as the International Searching Authority for International Application No. PCT/JP2016/058261.

Written Opinion (PCT/ISA/237) dated Jun. 7, 2016, by the Japanese Patent Office as the International Searching Authority for International Application No. PCT/JP2016/058261.

Extended European Search Report (EESR) dated Oct. 15, 2018, in European Application No. 16 768 569.2.

* cited by examiner

CATHETER AND MANUFACTURING METHOD OF CATHETER

CROSS-REFERENCES TO RELATED APPLICATIONS

This application is a continuation of International Application No. PCT/JP2016/058261 filed on Mar. 16, 2016, which claims priority to Japanese Application No. 2015-058537 filed on Mar. 20, 2015, the entire contents of which are incorporated herein by reference.

TECHNICAL FIELD

The present disclosure relates to a rapid exchange type catheter inserted into a living body lumen and a manufacturing method thereof.

BACKGROUND DISCUSSION

Vascular lesion treatment using a catheter is widely introduced since there is less surgical invasion. For example, in percutaneous transluminal coronary angioplasty, a balloon catheter is used to improve a blood flow by widening a lesion area of the coronary artery. In general, the balloon catheter has an elongated and hollow catheter shaft, a balloon disposed on a distal side of the catheter shaft, and a hub disposed on a proximal side of the catheter shaft.

As a structure of the balloon catheter, a known structure generally includes an over-the-wire type in which a guide wire is inserted from the proximal end into the distal of the catheter shaft and a rapid exchange type in which the guide wire is inserted into only the distal portion of the catheter shaft. In the rapid exchange type catheter, the guide wire is inserted into only the distal portion of the catheter shaft. Accordingly, a guide wire port for allowing the guide wire to pass therethrough is formed in an intermediate portion of the catheter shaft. A dilation lumen, which circulates a dilation fluid for dilating a balloon, is formed in the catheter shaft on the proximal side of the guide wire port. The dilation lumen and a guide wire lumen into which the guide wire is inserted are formed in parallel in the catheter shaft on the distal side of the guide wire port.

The catheter shaft having the guide wire port is manufactured as follows. First, a proximal side shaft, a distal side shaft, and an inner tube shaft are prepared. The inner tube shaft is inserted into a hollow interior of the distal side shaft. In a state where a proximal side terminal thereof is exposed from a proximal side terminal of the distal side shaft, the proximal side shaft, the distal side shaft, and the inner tube shaft are integrated with each other by means of thermal fusion-bonding. During the thermal fusion-bonding, core bar materials are respectively inserted into the hollow interior of the inner tube shaft serving as the guide wire lumen and the hollow interior of the distal side shaft serving as the dilation lumen. The respective shafts are fused using a thermally shrinkable tube.

When the catheter shaft is thermally fused, in order to restrain the guide wire lumen and the dilation lumen from communicating with each other or to prevent a portion between both of these from being thinned, a known technique is to dispose a connection tube in a proximal side end portion of the inner tube shaft, which forms the guide wire lumen. As the catheter having this catheter shaft, for example, JP-A-2014-195487 discloses a catheter.

SUMMARY

In order for the catheter shaft to satisfactorily pass through the inside of a living body lumen, it can be desirable to minimize an outer diameter of the catheter shaft as much as possible. On the other hand, if the proximal side end portion of the inner tube shaft is formed to become longer as described above, the outer diameter of the catheter shaft is likely to increase in the vicinity of a proximal opening portion of the guide wire lumen.

In accordance with an exemplary embodiment, a catheter and a manufacturing method thereof are disclosed, which can restrain a guide wire lumen and a dilation lumen from communicating each other during thermal fusion-bonding while suppressing an increase in an outer diameter of a catheter shaft.

In accordance with an exemplary embodiment, a catheter according to the present disclosure has a catheter shaft in which a distal side shaft that has a distal hollow portion, an inner tube shaft that is disposed inside the distal side shaft, and that has an inner tube hollow portion, and a proximal side shaft that has a proximal hollow portion communicating with the distal hollow portion are integrated with each other in a fusion region formed along an axial direction of the proximal side shaft. The inner tube shaft has an opening portion through which the inner tube hollow portion opens outward, and an arc-shaped portion which extends from the opening portion to a proximal side and which has only a portion of an entire circumference in a circumferential direction of the inner tube shaft. The fusion region includes the opening portion disposed on a distal side of a proximal end of the distal side shaft. A region in which the arc-shaped portion and the proximal side shaft are fused with each other is formed in the fusion region on the proximal side of opening portion. The proximal side shaft and the inner tube shaft are fused with each other over an entire length from the proximal portion to the distal portion of the fusion region.

In addition, a manufacturing method of a catheter according to the present disclosure includes a step of preparing a hollow distal side shaft, an inner tube shaft having an arc-shaped portion which can be disposed inside the distal side shaft and whose proximal portion has only a portion in an entire circumference in a circumferential direction, and a hollow proximal side shaft, a step of inserting the inner tube shaft into the distal side shaft, locating the arc-shaped portion of the inner tube shaft so as to be exposed from a proximal portion of the distal side shaft, locating the proximal side shaft so that a distal hollow portion of the distal side shaft and a proximal hollow portion of the proximal side shaft are continuous with each other and are adjacent to the arc-shaped portion, bringing a first core bar into a state where the first core bar is inserted into the inner tube hollow portion of the inner tube shaft from the proximal side, and bringing a second core bar into a state where the second core bar is inserted into the distal hollow portion of the distal side shaft from the proximal side, a step of disposing a thermally shrinkable tube so as to cover the distal side shaft and the proximal side shaft, and locating the distal position of the thermally shrinkable tube at a position which is on a distal side of a proximal position of the distal side shaft and a distal position of the arc-shaped portion of the inner tube shaft and a distal position of the proximal side shaft or on a proximal side of the distal position of the proximal side shaft, and a step of shrinking the thermally shrinkable tube by heating, and thermally fusing the distal side shaft, the inner tube shaft, and the proximal side shaft with each other.

In the catheter configured as described above, the proximal side shaft and the inner tube shaft are fused with each other over the entire length from the proximal portion to the distal portion of the fusion region. Accordingly, a thickness between the hollow portions of both the shafts can be sufficiently secured, and thus, it is possible to prevent both of the hollow portions from communicating with each other. In addition, the opening portion of the inner tube shaft is located on the distal side of the proximal end of the distal side shaft. Accordingly, a configuration can be adopted in which the outer diameter of the catheter shaft does not increase in the vicinity of the opening portion of the guide wire lumen. Furthermore, the arc-shaped portion belonging to the inner tube shaft is integrated with the proximal side shaft. Accordingly, a configuration can be adopted in which the outer diameter of the catheter shaft does not increase. In accordance with an exemplary embodiment, according to the present disclosure, the guide wire lumen and the dilation lumen can be restrained from communicating with each other during thermal fusion-bonding, while suppressing the increase in the outer diameter of the catheter shaft.

In accordance with an exemplary embodiment, a configuration may be adopted in which a distal position of the fusion region is a position which is on the distal side of the proximal position of the distal side shaft and the distal position of the arc-shaped portion of the inner tube shaft and the distal position of the proximal side shaft or on the proximal side of the distal position of the proximal side shaft. In this manner, a configuration can be adopted in which an entirety of the fusion region is included in a region where the inner tube shaft and the proximal side shaft overlap each other.

According to the manufacturing method of the catheter configured as described above, a tube wall of the inner tube shaft and a tube wall of the proximal side shaft are adjacent to and fused to each other over the entire length in the axial direction of the fusing range. Accordingly, the thickness between the first core bar and the second core bar can be sufficiently secured. In addition, the opening portion of the inner tube shaft is located on the distal side of the proximal end of the distal side shaft. Accordingly, a configuration can be adopted in which the outer diameter of the catheter shaft does not increase in the vicinity of the opening portion of the guide wire lumen. Furthermore, the proximal side end portion of the inner tube shaft is the arc-shaped portion having only a portion in the circumferential direction. In this manner, the increases in the outer diameter of the catheter shaft in the region where the inner tube shaft and the proximal side shaft are joined together can be suppressed.

The distal side shaft may have a distal side slit portion through which the proximal side shaft is inserted into a proximal side end portion, along an axial direction. When the thermally shrinkable tube is disposed, the distal position of the thermally shrinkable tube may be located at a distal position of the distal side slit portion or a position on the distal side of the distal position of the distal side slit portion. In this manner, the proximal side shaft can be inserted into a hollow interior of the distal side shaft so as to be adjacent to the inner tube shaft over the entire length of the fusion region. Accordingly, the distal side shaft and the proximal side shaft can be easily continuous with each other. In addition, the entire length of the distal side slit portion is included inside the fusion region. Accordingly, the distal side slit portion can be closed by fusing the shafts with each other.

The proximal side shaft may have a proximal side slit portion through which the distal side shaft is inserted into a distal side end portion, along the axial direction. A configuration may be adopted in which when the thermally shrinkable tube is disposed, the distal position of the thermally shrinkable tube is located so as to be a distal position of the proximal side slit portion or a position on the distal side of the distal position of the distal side slit portion. In this manner, the proximal side shaft can be inserted into a hollow interior of the distal side shaft so as to be adjacent to the inner tube shaft over the entire length of the fusion region. Accordingly, the distal side shaft and the proximal side shaft can be easily continuous with each other. In addition, the entire length of the proximal side slit portion is included inside the fusion region. Accordingly, the proximal side slit portion can be closed by fusing the shafts with each other.

A configuration may be adopted in which the arc-shaped portion of the inner tube shaft is formed to be smaller than a half of the entire circumference of the inner tube shaft in the circumferential direction. In this manner, it is possible to effectively suppress the increase in the outer diameter of the catheter shaft after the inner tube shaft and the proximal side shaft are fused with each other.

The proximal side shaft may be cut in a slope shape from the distal side toward the proximal side. When a hollow portion of the distal side shaft and a hollow portion of the proximal side shaft are located so as to be continuous with each other, a region including the most distal portion in the circumferential direction of the proximal side shaft may be located so as to be adjacent to the inner tube shaft. In this manner, the most distal portion of the proximal side shaft is located on the distal side of the fusion region. Accordingly, a state where the inner tube shaft and the proximal side shaft overlap each other over the entire length of the fusion region can be reliably ensured. In addition, the proximal side shaft is cut in the slope shape from the distal side toward the proximal side. Accordingly, the increase in the outer diameter of the catheter shaft can be effectively suppressed.

In accordance with an exemplary embodiment, a configuration may be adopted in which when the thermally shrinkable tube is disposed, the proximal position of the thermally shrinkable tube is located so as to be the proximal position of the arc-shaped portion. In this manner, fusing work can be carried out for a required and sufficient region.

A manufacturing method of a catheter is disclosed, comprising: preparing a hollow distal side shaft and an inner tube shaft having an arc-shaped portion which can be disposed inside the distal side shaft, the inner tube shaft having a proximal portion having a circumference which is less than a half of an entire circumference in a circumferential direction, and a hollow proximal side shaft; inserting the inner tube shaft into the distal side shaft, locating the arc-shaped portion of the inner tube shaft so as to be exposed from a proximal portion of the distal side shaft, locating the proximal side shaft so that a distal hollow portion of the distal side shaft and a proximal hollow portion of the proximal side shaft are continuous with each other and are adjacent to the arc-shaped portion, bringing a first core bar into a state where the first core bar is inserted into the inner tube hollow portion of the inner tube shaft from the proximal side, and bringing a second core bar into a state where the second core bar is inserted into the distal hollow portion of the distal side shaft from the proximal side; disposing a thermally shrinkable tube so as to cover the distal side shaft and the proximal side shaft, and locating the distal position of the thermally shrinkable tube at a position which is on a distal side of a proximal position of the distal side shaft and a distal position of the arc-shaped portion of the inner tube shaft and at a distal position of the proximal side shaft or on a proximal side of the distal position of the proximal side shaft; and thermally fusing the distal side shaft, the inner tube shaft, and the proximal side shaft with each other by shrinking the thermally shrinkable tube.

DETAILED DESCRIPTION

Figure 1:
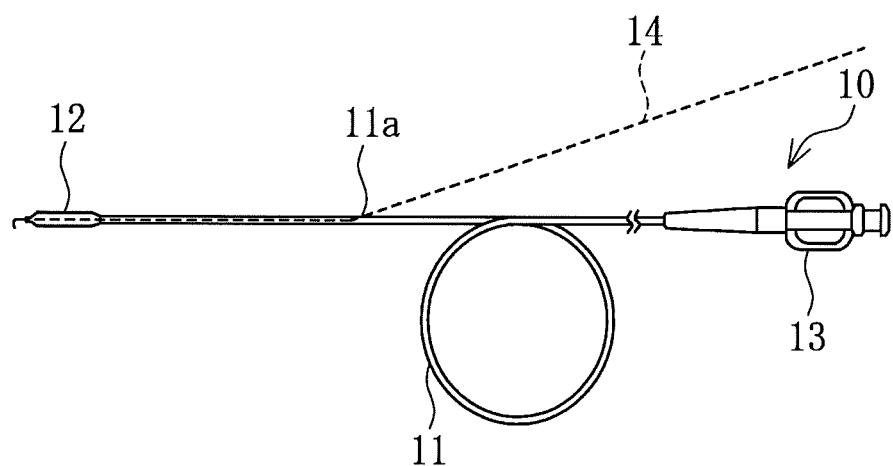
FIG. 1 is a front view of a catheter according to the present embodiment.

Hereinafter, an embodiment according to the present disclosure will be described with reference to the drawings. Note that in some cases, a dimension ratio in the drawings may be exaggerated and different from a ratio used in practice in order to facilitate the description. In addition, in the description herein, a side of a balloon catheter 10 which is inserted into a living body lumen is referred to as a "distal end" or a "distal side", and an operating hand side is referred to as a "proximal end" of a "proximal side".

First, a configuration of the balloon catheter 10 will be described. As illustrated in FIG. 1, the balloon catheter 10 has an elongated and hollow catheter shaft 11, a balloon 12 disposed in a distal side end portion of the catheter shaft 11, and a hub 13 fixedly attached to a proximal side end portion of the catheter shaft 11.

In the balloon catheter 10, the elongated catheter shaft 11 is inserted into a living body organ, and the balloon 12 disposed on the distal side is dilated in a lesion area. In this manner, the lesion area can be widened and treated. An opening portion 11a to which the guide wire 14 is introduced is disposed close to the distal side of the catheter shaft 11. In accordance with an exemplary embodiment, the balloon catheter 10 is a so-called rapid exchange type catheter.

As a material the catheter shaft 11, a flexible material can be used. For example, polyethylene, polypropylene, polybutene, ethylene-propylene copolymer, ethylene-vinyl acetate copolymer, ionomer, or polyolefin such as mixtures of two or more thereof, soft polyvinyl chloride resin, polyamide, polyamide elastomer, polyester, polyester elastomer, polyurethane, fluorine resin such as Polytetrafluoroethylene can be used.

Figure 2:
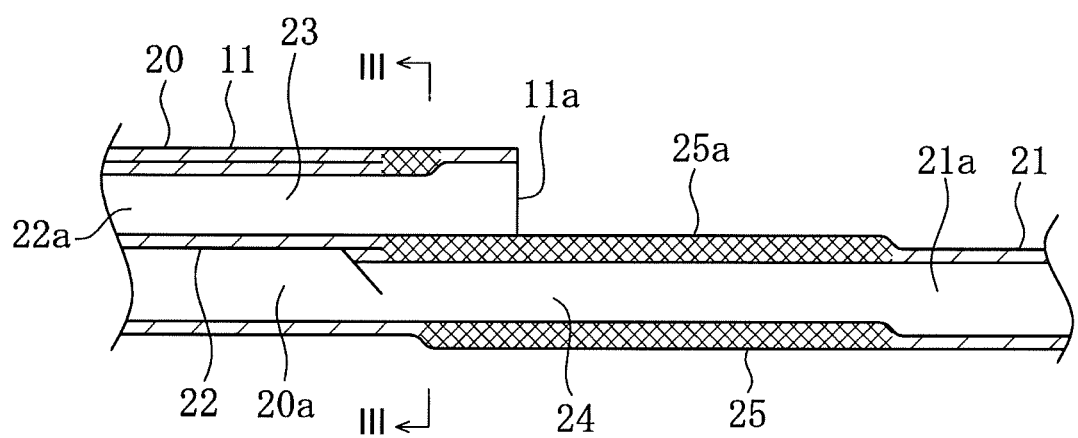
FIG. 2 is an enlarged cross-sectional view illustrating the vicinity of a joint portion of a catheter shaft.

Next, a structure in the vicinity of the opening portion 11a of the catheter shaft 11 will be described. As illustrated in FIG. 2, in the vicinity of the opening portion 11a of the catheter shaft 11, the distal side shaft 20, the proximal side shaft 21, and the inner tube shaft 22 are integrated with each other in a fusion region 25. Note that the fusion region 25 is shaded and illustrated in FIG. 2.

Note that the proximal side shaft 21 may have a plurality of the shafts, which are joined to each other in the axial direction. In this case, for example, the proximal portion of the proximal side shaft 21 is formed of a metal material such as stainless steel or aluminum. The distal portion of the proximal side shaft 21 may be formed of the above-described resin material.

In accordance with an exemplary embodiment, the inner tube shaft 22 having an inner tube hollow portion 22a along the axial direction is accommodated inside the distal side shaft 20 having a distal hollow portion 20a along the axial direction. In addition, a portion of the distal hollow portion 20a other than the inner tube shaft 22 is continuous with a proximal hollow portion 21a belonging to the proximal side shaft 21.

The inner tube hollow portion 22a communicates with the outside by the opening portion 11a of the proximal portion, and forms a guide wire lumen 23 into which the guide wire 14 is inserted. In addition, the proximal hollow portion 21a and the distal hollow portion 20a continuous therewith communicate with the balloon 12, and form a dilation lumen 24, which circulates a dilation fluid. The dilation fluid for dilating the balloon 12 may be gas or liquid. For example, gas such as helium gas, $CO_2$ gas, $O_2$ gas, or liquid such as a physiological salt solution and a contrast agent can be used.

The fusion region 25 has a portion where the distal side shaft 20 and the proximal side shaft 21 are overlapped and fused with each other, a portion where the distal side shaft 20 and the inner tube shaft 22 are overlapped and fused with each other, and a portion where the proximal side shaft 21 and the inner tube shaft 22 are overlapped and fused with each other. That is, tube walls of the two shafts are overlapped and fused with each other. Therefore, the wall thickness is correspondingly increased.

In a state before being fused, the proximal side end portion of the inner tube shaft 22 has an inner tube arc-shaped portion 40 having only a portion of the entire circumference in the circumferential direction of the inner tube shaft 22. Note that the inner tube arc-shaped portion 40 will be described in detail with reference to a manufacturing method of the catheter 10. The inner tube shaft 22 and the proximal side shaft 21 are fused with each other, thereby forming a region where the inner tube arc-shaped portion 40 belonging to the inner tube shaft 22 and the proximal side shaft 21 are fused with each other. Including this region, the proximal side shaft 21 and the inner tube shaft 22 are fused with each other in a region 25a over the entire length from the proximal portion to the distal portion of the fusion region 25.

The proximal position of the portion having the entire circumference in the inner tube shaft 22 is located on the distal side of the proximal position of the distal side shaft 20. In addition, the inner tube arc-shaped portion 40 is fused with the proximal side shaft 21. Accordingly, the portion formed by the distal side shaft 20 in the opening portion 11a is thinner than the fusion region 25.

Figure 3:
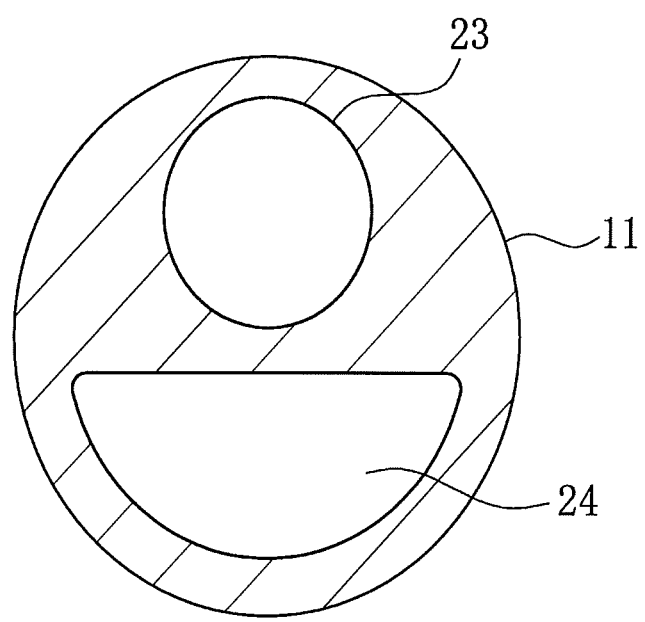
FIG. 3 is a cross-sectional view taken along line III-Ill in FIG. 2.

As illustrated in FIG. 3, the catheter shaft 11 is integrated with the portion where the distal side shaft 20, the proximal side shaft 21, and the inner tube shaft 22 are fused with each other. The outer diameter of the catheter shaft 11 is substantially circular. The guide wire lumen 23 having a substantially circular shape is formed on one side in the radial direction. The dilation lumen 24 having a substantially semicircular shape is formed on the other side in the radial direction. In the dilation lumen 24, a substantially semicircular chord portion faces the guide wire lumen 23. The guide wire lumen 23 and the dilation lumen 24 are arranged separate from each other inside the catheter shaft 11.

In the fusion region 25, the proximal side shaft 21 and the inner tube shaft 22 are fused with each other over the entire length from the proximal portion to the distal portion. Accordingly, the thickness between the guide wire lumen 23 and the dilation lumen 24 can be sufficiently secured, and it is possible to prevent both of these from communicating with each other.

In addition, on the proximal side of the opening portion 11a, the inner tube shaft 22 has the inner tube arc-shaped portion 40 formed in only the portion in the circumferential direction, and the inner tube arc-shaped portion 40 is integrated with the proximal side shaft 21. Accordingly, an increase in the outer diameter on the proximal side from the opening portion 11a of the catheter shaft 11 can be suppressed.

Figure 4:
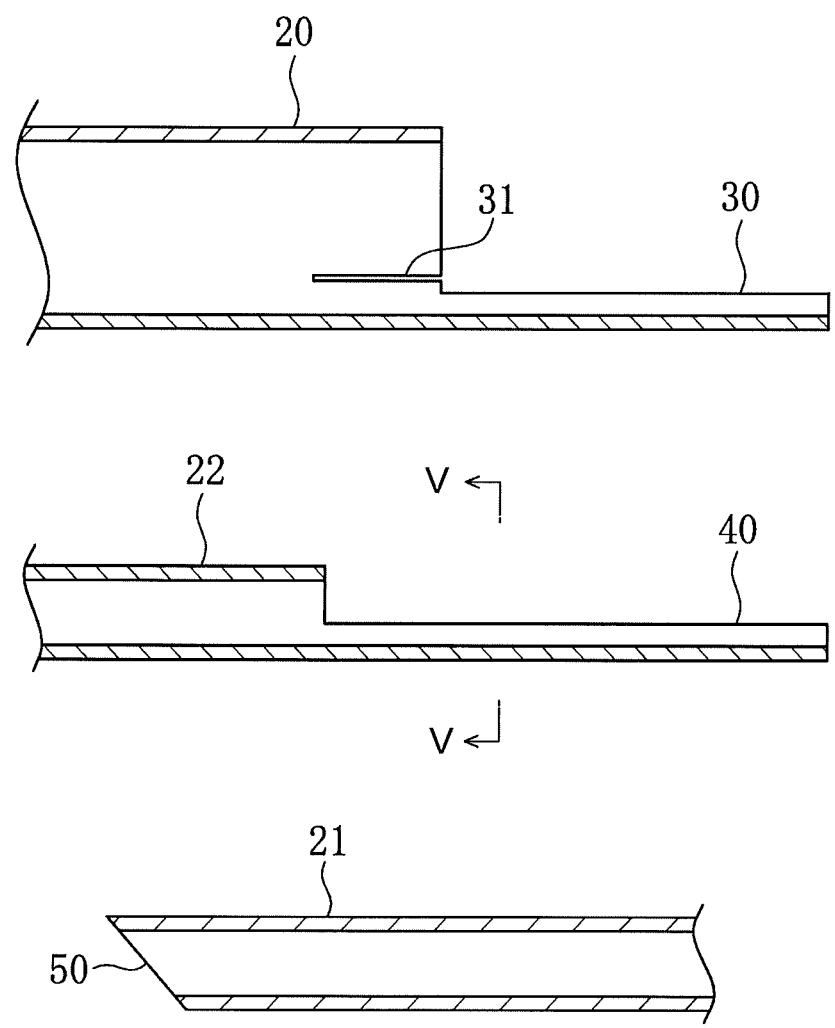
FIG. 4 is a cross-sectional view of three shafts, which form the catheter shaft.

Next, a manufacturing method of the catheter 10, for example, a manufacturing method of the catheter shaft 11 having the above-described structure in the vicinity of the opening portion 11a will be described. As illustrated in FIG. 4, first, the distal side shaft 20, the inner tube shaft 22, and the proximal side shaft 21 which form the catheter shaft 11 are prepared.

The distal side shaft 20 is formed in a tubular shape having the distal hollow portion 20a along the axial direction. In addition, the proximal side end portion of the distal side shaft 20 has a distal shaft arc-shaped portion 30 in which only a portion in the circumferential direction of the entire circumference extends toward the proximal side. In addition, the distal side shaft 20 has a distal side slit portion 31, which extends from the proximal side end surface toward the distal side. The distal side slit portion 31 is also disposed at a symmetrical position when the distal side shaft 20 is viewed from the opposite side in a cross section the same as that of FIG. 4.

Figure 5:
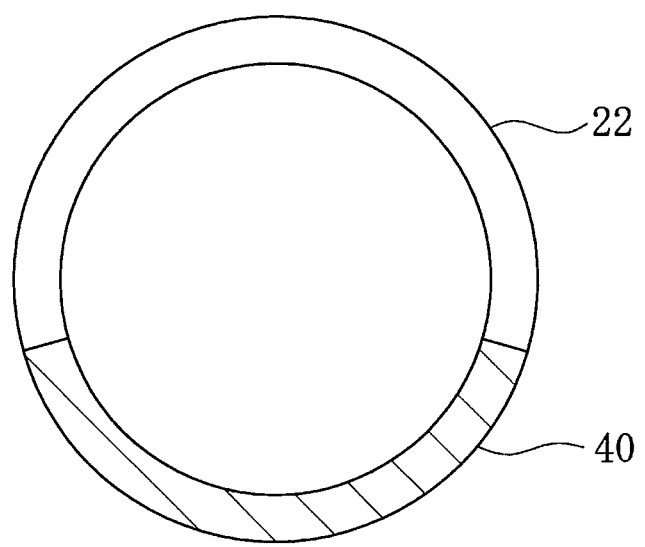
FIG. 5 is a cross-sectional view taken along line V-V in FIG. 4.

The inner tube shaft 22 is formed in a tubular shape having the inner tube hollow portion 22a along the axial direction. In addition, the proximal side end portion of the inner tube shaft 22 has an inner tube arc-shaped portion 40 in which only a portion in the circumferential direction of the entire circumference extends toward the proximal side. As illustrated in FIG. 5, for example, the inner tube arc-shaped portion 40 is formed so as to cross the region, which is smaller than a half the entire circumference of the inner tube shaft 22. Note that in accordance with an exemplary embodiment, the distal shaft arc-shaped portion 30 also has the same configuration.

The proximal side shaft 21 is formed in a tubular shape having the proximal hollow portion 21a along the axial direction. In addition, the proximal side shaft 21 has a slope-shaped distal surface 50 formed by cutting the distal side end portion into a slope shape.

Figure 6:
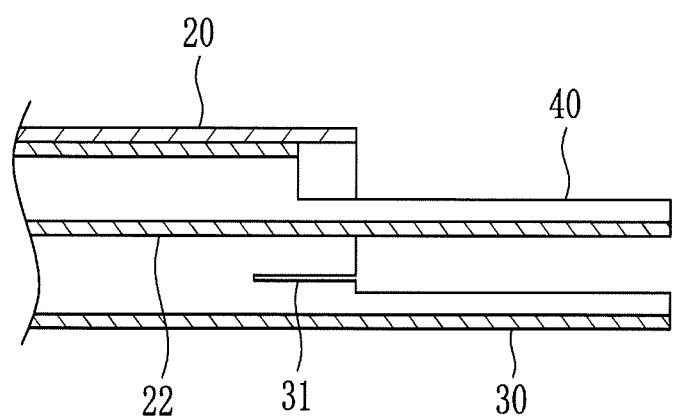
FIG. 6 is a cross-sectional view illustrating a state where an inner tube shaft is accommodated inside a distal side shaft.

In accordance with an exemplary embodiment, before the respective shafts are joined to each other, the respective shafts are located at each predetermined position. First, the inner tube shaft 22 is accommodated inside the distal side shaft 20. As illustrated in FIG. 6, the inner tube shaft 22 is accommodated inside the distal hollow portion 20a of the distal side shaft 20. The inner tube arc-shaped portion 40 of the inner tube shaft 22 is located so as to be exposed from the proximal side end portion toward the proximal side of the distal side shaft 20. The proximal position of the inner tube arc-shaped portion 40 is located so as to substantially coincide with the proximal position of the distal shaft arc-shaped portion 30 of the distal side shaft 20 in the axial direction.

In addition, in the circumferential direction, the inner tube arc-shaped portion 40 is located so as to face a side on which the proximal side shaft 21 is located later. The proximal position of the tubular portion having the entire circumference in the inner tube shaft 22 is located in the hollow interior of the distal side shaft 20 and on the proximal side of the distal position of the distal side slit portion 31. Note that in this located state, the inner tube shaft 22 may be fixedly attached to the distal side shaft 20 on the distal side (not illustrated).

Figure 7:
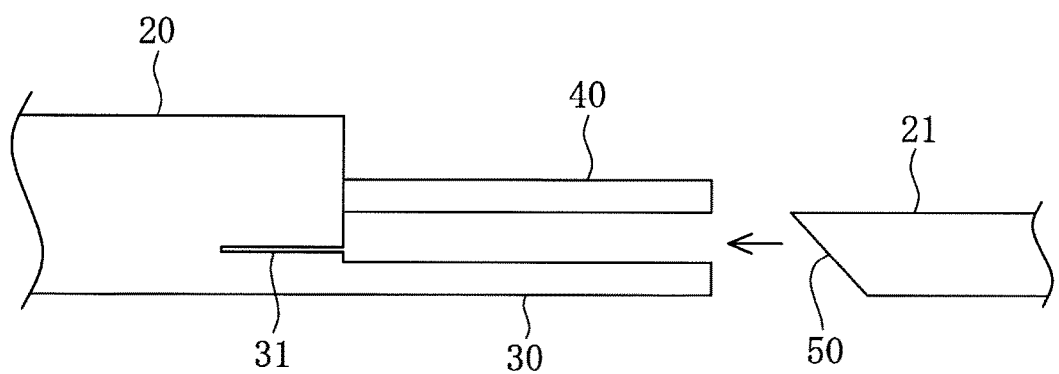
FIG. 7 is a front view illustrating a position and a direction of a proximal side shaft inserted into the distal side shaft, which accommodates the inner tube shaft.

Next, the proximal side shaft 21 is caused to be continuous with the distal side shaft 20. As illustrated in FIG. 7, the distal side of the proximal side shaft 21 is inserted into the proximal portion of the distal side shaft 20. In this case, the distal shaft arc-shaped portion 30 of the distal side shaft 20 is inserted into the hollow interior of the proximal side shaft 21. In addition, the proximal side shaft 21 is inserted in the circumferential direction where the region including the most distal portion in the circumferential direction of the slope-shaped distal surface 50 becomes adjacent to the inner tube shaft 22.

In accordance with an exemplary embodiment, the proximal side shaft 21 is inserted so as to fit into the distal side slit portion 31 of the distal side shaft 20. In this manner, in the circumferential direction of the proximal side shaft 21, the region including the most distal portion is located in the hollow interior of the distal side shaft 20. The other region is exposed outward from the distal side shaft 20 via the distal side slit portion 31.

Figure 8:
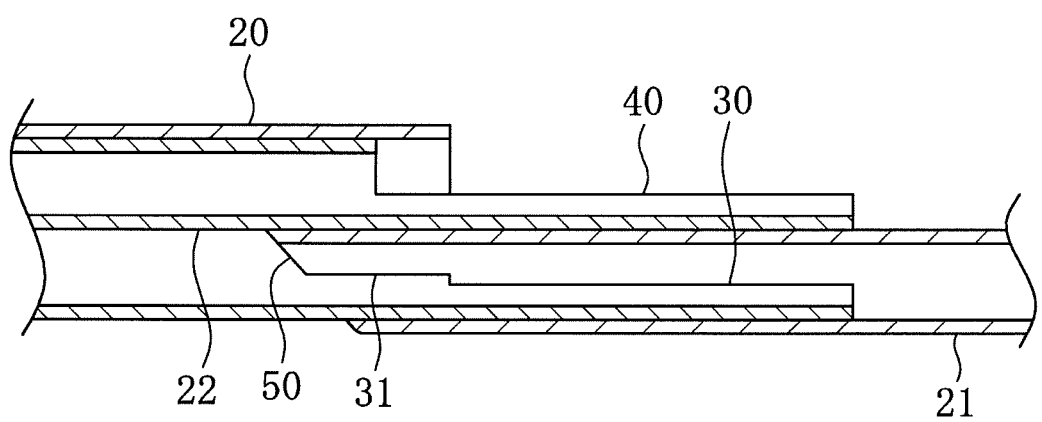
FIG. 8 is a cross-sectional view illustrating a state where the proximal side shaft is accommodated inside the distal side shaft.
Figure 9:
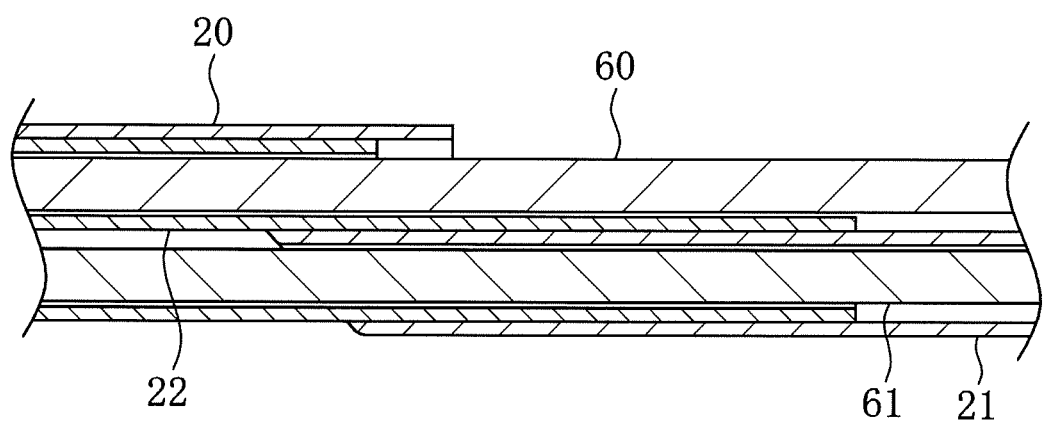
FIG. 9 is a cross-sectional view illustrating a state where a first core bar is inserted into an inner tube hollow portion and a second core bar is inserted into a proximal hollow portion and a distal hollow portion.

As illustrated in FIG. 8, the proximal side shaft 21 overlaps the inner tube shaft 22 from the distal position to the proximal position of the inner tube arc-shaped portion 40. In addition, the distal shaft arc-shaped portion 30 also overlaps the proximal side shaft 21. After the respective shafts are arranged in this way, as illustrated in FIG. 9, the first core bar 60 is inserted into the inner tube hollow portion 22a of the inner tube shaft 22, and the second core bar 61 is inserted into the proximal hollow portion 21a of the proximal side shaft 21 and the distal hollow portion 20a of the distal side shaft 20. The first core bar 60 has a cross sectional shape of the guide wire lumen 23 illustrated in FIG. 3, and the second core bar 61 has a cross sectional shape of the dilation lumen 24 illustrated in FIG. 3.

Next, the thermally shrinkable tube 26 is disposed in the outer periphery of the joint portion of the respective shafts. For example, the thermally shrinkable tube 26 is formed of a material such as polyolefin. The thermally shrinkable tube 26 shrinks when heated, and the diameter after heated is smaller than the diameter before heated. Therefore, the thermally shrinkable tube 26 is heated, thereby enabling the distal side shaft 20, the proximal side shaft 21, and the inner tube shaft 22 to be pressurized inward from the outside.

Figure 10:
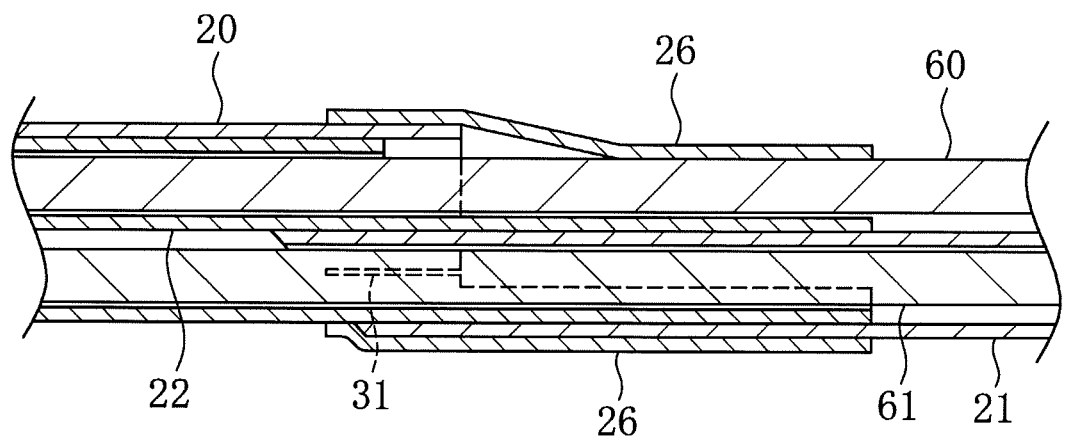
FIG. 10 is a cross-sectional view illustrating a state where a thermally shrinkable tube is disposed in the state illustrated in FIG. 9.

As illustrated in FIG. 10, the distal position of the thermally shrinkable tube 26 is located on the distal side of the proximal position of the inner tube shaft 22 except for the inner tube arc-shaped portion 40 and on the proximal side of the most distal position of the proximal side shaft 21. In addition, the distal position of the thermally shrinkable tube 26 is located at the same position as the distal position of the distal side slit portion 31 formed in the distal side shaft 20, or a position on the slightly distal side of the distal side slit portion 31 in the distal side shaft 20. The proximal position of the thermally shrinkable tube 26 is located so as to be substantially the same position as the proximal position of the distal shaft arc-shaped portion 30 of the distal side shaft 20 and the proximal position of the inner tube arc-shaped portion 40 of the inner tube shaft 22.

In accordance with an exemplary embodiment, the joint portion of the shafts is heated in a state illustrated in FIG. 10. In this manner, the thermally shrinkable tube 26 shrinks, and the diameter of the thermally shrinkable tube 26 decreases. In this case, the distal side shaft 20, the proximal side shaft 21, and the inner tube shaft 22 are respectively softened. Tube walls adjacent to each other are fused and integrated with each other.

Figure 11:
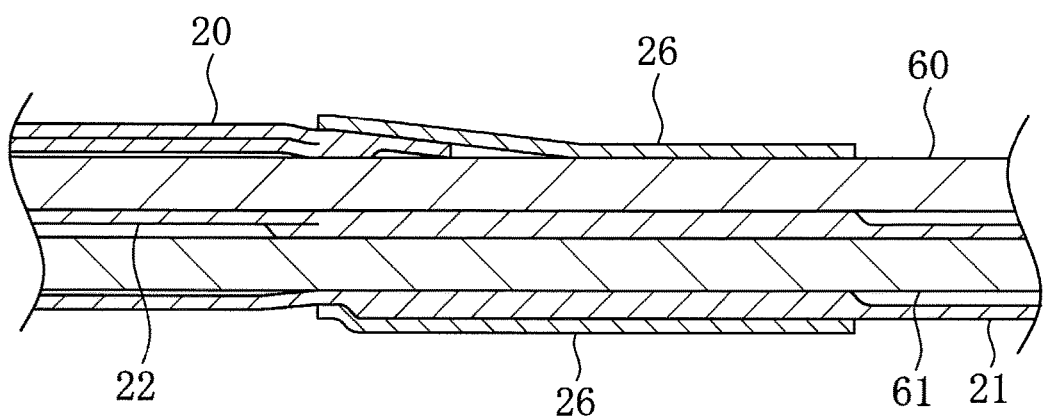
FIG. 11 is a cross-sectional view illustrating a state where the thermally shrinkable tube is shrunk by being heated in the state illustrated in FIG. 10.

As illustrated in FIG. 11, the distal side shaft 20 and the proximal portion of the inner tube shaft 22 are interposed and pressurized between the thermally shrinkable tube 26 and the first core bar 60. In this manner, the distal side shaft 20 and the proximal portion of the inner tube shaft 22 are fused with each other. In addition, the inner tube shaft 22 and the proximal side shaft 21 are interposed and pressurized between the first core bar 60 and the second core bar 61. In this manner, the inner tube shaft 22 and the proximal side shaft 21 are fused with each other. Furthermore, the distal side shaft 20 and the proximal side shaft 21 are interposed and pressurized between the thermally shrinkable tube 26 and the second core bar 61. In this manner, both of the distal side shaft 20 and the proximal side shaft 21 are fused with each other. In addition, the distal position of the thermally shrinkable tube 26 is located at the same position as the distal position of the distal side slit portion 31 of the distal side shaft 20 or at the position on the slightly distal side therefrom. Accordingly, the distal side slit portion 31 is closed over the entire length by the fusing.

The tube wall of the inner tube shaft 22 and the tube wall of the proximal side shaft 21 are adjacent to and fused with each other over the entire length in the axial direction of the fusing range. Accordingly, it is possible to secure a sufficient thickness between the first core bar 60 and the second core bar 61. In addition, the proximal side end portion of the inner tube shaft 22 is the inner tube arc-shaped portion 40 having only a portion in the circumferential direction. In this manner, it is possible to suppress an increase in the outer diameter of the catheter shaft 11 in the region where the inner tube shaft 22 and the proximal side shaft 21 are joined together.

In addition, in the manufacturing method according to the present embodiment, the distal portion of the proximal side shaft 21 is cut into a slope shape, and a portion including the most distal portion is located so as to be adjacent to the inner tube shaft 22. Accordingly, the proximal side shaft 21 extends to the distal side of the fusion region 25a fused with the inner tube shaft 22. In the fusion region 25a within the range where the thermally shrinkable tube 26 is provided, both of these can be reliably brought into a state adjacent to each other. Therefore, the thickness between the first core bar 60 and the second core bar 61 can be reliably secured. Furthermore, the distal side shaft 20 has the distal shaft arc-shaped portion 30, and overlaps the distal portion of the proximal side shaft 21. In this manner, it is also possible to secure a sufficient thickness in the fusing portion between the distal side shaft 20 and the proximal side shaft 21, and it is possible to eliminate a possibility that a thin portion may be formed. Therefore, the strength of the joint portion of the catheter shaft 11 can be sufficiently secured.

After the fusing process is performed, the thermally shrinkable tube 26 is removed, and the first core bar 60 and the second core bar 61 are detached. In this manner, the catheter shaft 11 having the joint portion of the shafts as illustrated in FIG. 2 can be manufactured. The catheter 10 is manufactured by further attaching the balloon 12 or the hub 13 to the catheter shaft 11.

Figure 12:
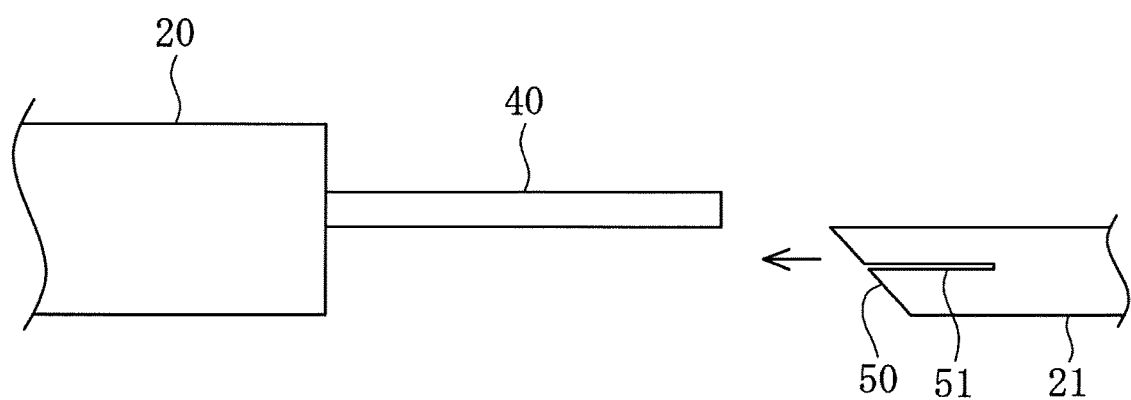
FIG. 12 is an exploded front view of a distal side shaft and a proximal side shaft according to a first modification example.

Next, a modification example of the distal side shaft 20 and the proximal side shaft 21 will be described. As illustrated in FIG. 12, in this modification example, the distal side shaft 20 does not have the distal shaft arc-shaped portion. In this way, the distal side shaft 20 may not necessarily have the distal shaft arc-shaped portion.

In addition, in this modification example, the distal side shaft 20 does not have a slit portion. Alternatively, the proximal side shaft 21 has a proximal side slit portion 51 from the distal portion toward the proximal side. The proximal side slit portion 51 has the same axial length as that of the distal side slit portion 31 belonging to the distal side shaft 20 in FIG. 4. The proximal side shaft 21 has the proximal side slit portion 51. Accordingly, the portion including the most distal portion of the proximal side shaft 21 is accommodated in the hollow interior of the distal side shaft 20. A portion on the opposite side across the proximal side slit portion 51 can be exposed outward from the distal side shaft 20. In this case, the distal position of the thermally shrinkable tube 26 is located at the same position as the distal position of the proximal side slit portion 51 of the proximal side shaft 21 inserted into the distal side shaft 20 or at the position on the slightly distal side therefrom.

Figure 13:
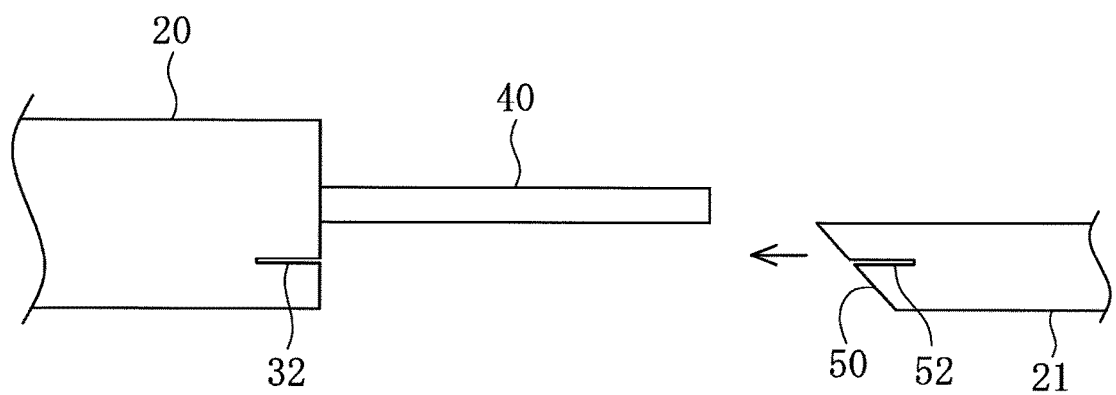
FIG. 13 is an exploded front view of a distal side shaft and a proximal side shaft according to a second modification example.

As illustrated in FIG. 13, a distal side slit portion 32 may be formed in the distal side shaft 20, and a proximal side slit portion 52 may be formed in the proximal side shaft 21. In this case, the combined length of the distal side slit portion 32 and the proximal side slit portion 52 may be the same axial length as that of the distal side slit portion 31 belonging to the distal side shaft 20 in FIG. 4. In addition, the distal position of the thermally shrinkable tube 26 in this case is located at the same position as the distal position of the proximal side slit portion 52 of the proximal side shaft 21 inserted into the distal side shaft 20 or at the position on the slightly distal side therefrom.

As described above, the catheter 10 according to the present embodiment has the catheter shaft 11 in which the distal side shaft 20 that has the distal hollow portion 20a, the inner tube shaft 22 that is disposed inside the distal side shaft 20, and that has the inner tube hollow portion 22a, and the proximal side shaft 21 that has the proximal hollow portion 21a communicating with the distal hollow portion 20a are integrated with each other in the fusion region 25 formed along the axial direction of the proximal side shaft 21. The inner tube shaft 22 has the opening portion 11a in which the inner tube hollow portion 22a opens outward, and the arc-shaped portion 40 which extends to the proximal side from the opening portion 11a and which has only a portion of the entire circumference in the circumferential direction of the inner tube shaft 22. In accordance with an exemplary embodiment, the fusion region 25 includes the opening portion 11a disposed on the distal side of the proximal end of the distal side shaft 20. The region in which the arc-shaped portion 40 and the proximal side shaft 21 are fused with each other is formed in the fusion region 25 on the proximal side of the opening portion 11a. The proximal side shaft 21 and the inner tube shaft 22 are fused with each other over the entire length from the proximal portion to the distal portion of the fusion region 25. In this manner, the proximal side shaft 21 and the inner tube shaft 22 are fused with each other over the entire length from the proximal portion to the distal portion of the fusion region 25. Accordingly, a sufficient wall thickness between the hollow portions of both shafts can be secured, and it is possible to prevent both of these from communicating with each other. In addition, the opening portion 11a of the inner tube shaft 22 is located on the distal side of the proximal end of the distal side shaft 20. Accordingly, the outer diameter of the catheter shaft 11 cannot be increased in the vicinity of the opening portion of the guide wire lumen 23. Furthermore, the arc-shaped portion 40 belonging to the inner tube shaft 22 is integrated with the proximal side shaft 21. Accordingly, the outer diameter of the catheter shaft 11 cannot be increased. That is, according to the present disclosure, the guide wire lumen 23 and the dilation lumen 24 can be restrained from communicating with each other during thermal fusion-bonding, while suppressing the increase in the outer diameter of the catheter shaft 11.

In addition, in accordance with an exemplary embodiment, if the distal position of the fusion region 25 is located at a position which is on the distal side of the proximal position of the distal side shaft 20 and the distal position of the arc-shaped portion 40 of the inner tube shaft 22 and the distal position of the proximal side shaft 21 or on the proximal side of the distal position of the proximal side shaft 21, all of the fusion region 25 can be included in the region where the inner tube shaft 22 and the proximal side shaft 21 overlap each other.

In addition, the manufacturing method of the catheter according to the present embodiment has a step of preparing the hollow distal side shaft 20, the inner tube shaft 22 having the arc-shaped portion 40 which can be disposed inside the distal side shaft 20 and whose proximal portion has only a portion in the entire circumference in the circumferential direction, and the hollow proximal side shaft 21, a step of inserting the inner tube shaft 22 into the distal side shaft 20, locating the arc-shaped portion 40 of the inner tube shaft 22 so as to be exposed from the proximal portion of the distal side shaft 20, locating the proximal side shaft 21 so that the distal hollow portion 20a of the distal side shaft 20 and the proximal hollow portion 21a of the proximal side shaft 21 are continuous with each other and are adjacent to the arc-shaped portion 40, bringing the first core bar 60 into a state where the first core bar 60 is inserted into the inner tube hollow portion 22a of the inner tube shaft 22 from the proximal side, and bringing the second core bar 61 into a state where the second core bar 61 is inserted into the distal hollow portion 20a of the distal side shaft 20 from the proximal side, a step of disposing the thermally shrinkable tube 26 so as to cover the distal side shaft 20 and the proximal side shaft 21, and locating the distal position of the thermally shrinkable tube 26 at a position which is on the distal side of the proximal position of the distal side shaft 20 and the distal position of the arc-shaped portion 40 of the inner tube shaft 22 and the distal position of the proximal side shaft 21 or on the proximal side of the distal position of the proximal side shaft 21, and a step of shrinking the thermally shrinkable tube 26 by heating, and thermally fusing the distal side shaft 20, the inner tube shaft 22, and the proximal side shaft 21 with each other. In this manner, the tube wall of the inner tube shaft 22 and the tube wall of the proximal side shaft 21 are adjacent to and fused with each other over the entire axial length of the fusing range.

Accordingly, a sufficient thickness between the first core bar 60 and the second core bar 61 can be secured. In addition, the opening portion 11a of the inner tube shaft 22 is located on the distal side of the proximal end of the distal side shaft 20. Accordingly, the outer diameter of the catheter shaft 11 cannot be increased in the vicinity of the opening portion of the guide wire lumen 23. Furthermore, the proximal side end portion of the inner tube shaft 22 is the arc-shaped portion 40 having only a portion in the circumferential direction. In this manner, an increase in the outer diameter of the catheter shaft 11 in the region where the inner tube shaft 22 and the proximal side shaft 21 are joined together can be suppressed.

In addition, the distal side shaft 20 has the distal side slit portion 31 through which the proximal side shaft 21 is inserted into the proximal side end portion, along an axial direction. When the thermally shrinkable tube 26 is provided, if the distal position of the thermally shrinkable tube 26 is located at the distal position of the distal side slit portion 31 or the position on the distal side of the distal position of the distal side slit portion 31, the proximal side shaft 21 can be inserted into the hollow interior of the distal side shaft 20 so as to be adjacent to the inner tube shaft 22 over the entire length of the fusion region 25. The distal side shaft 20 and the proximal side shaft 21 can be easily continuous with each other. In addition, the entire length of the distal side slit portion 31 is included in the fusion region 25. Accordingly, the distal side slit portion 31 can be closed by fusing the shafts with each other.

In addition, the proximal side shaft 21 has the proximal side slit portion 51 through which the distal side shaft 20 is inserted into the distal side end portion, along an axial direction. When the thermally shrinkable tube 26 is provided, if the distal position of the thermally shrinkable tube 26 is located at the distal position of the proximal side slit portion 51 or the position on the distal side of the distal position of the proximal side slit portion 51, the proximal side shaft 21 can be inserted into the hollow interior of the distal side shaft 20 so as to be adjacent to the inner tube shaft 22 over the entire length of the fusion region 25. The distal side shaft 20 and the proximal side shaft 21 can be easily continuous with each other. In addition, the entire length of the proximal side slit portion 51 is included in the fusion region 25. Accordingly, the proximal side slit portion 51 can be closed by fusing the shafts with each other.

In addition, if the arc-shaped portion 40 of the inner tube shaft 22 is formed to be smaller than the half of the circumference of the inner tube shaft 22 in the circumferential direction, an increase in the outer diameter of the catheter shaft 11 after the inner tube shaft 22 and the proximal side shaft 21 are fused with each other can be effectively suppressed.

In addition, the proximal side shaft 21 is cut into a slope shape from the distal side toward the proximal side. When the hollow portion of the distal side shaft 20 and the hollow portion of the proximal side shaft 21 are located so as to be continuous with each other, if the region including the most distal portion in the circumferential direction of the proximal side shaft 21 is located so as to be adjacent to the inner tube shaft 22, the most distal portion of the proximal side shaft 21 is located on the distal side of the fusion region 25. Accordingly, a state where the inner tube shaft 22 and the proximal side shaft 21 overlap each other over the entire length of the fusion region 25 can be reliably ensured. In addition, the proximal side shaft 21 is cut into a slope shape from the distal side toward the proximal side. Accordingly, an increase in the outer diameter of the catheter shaft 11 can be effectively suppressed.

In addition, when the thermally shrinkable tube 26 is provided, if the proximal position of the thermally shrinkable tube 26 is located at the proximal position of the arc-shaped portion 40, fusing work can be carried out for a required and sufficient region.

Note that the present disclosure is not limited to only the above-described embodiment, and various modifications can be made by those skilled in the art within the technical idea of the present disclosure. For example, in the above embodiment, the slope-shaped distal surface 50 is formed in the distal portion of the proximal side shaft 21. However, the distal end of the proximal side shaft 21 may not have the slope shape, and may be formed to have a distal surface having a plane orthogonal to the axial direction. Even in this case, the distal position of the fusion region 25 is located at the distal position of the distal side slit portion 31 or the proximal side slit portion 51 or the position on the slightly distal side therefrom.

The detailed description above describes a rapid exchange type catheter inserted into a living body lumen and a manufacturing method thereof. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter comprising:
a catheter shaft in which a distal side shaft that has a distal hollow portion, an inner tube shaft that is disposed inside the distal side shaft, and that has an inner tube hollow portion, and a proximal side shaft that has a proximal hollow portion communicating with the distal hollow portion are integrated with each other in a fusion region formed along an axial direction of the proximal side shaft;
the inner tube shaft having an opening portion through which the inner tube hollow portion opens outward, and an arc-shaped portion which extends along the axial direction from the opening portion to a proximal side and which has only a portion of an entire circumference in a circumferential direction of the inner tube shaft, and wherein the arc-shaped portion is parallel with a center axis of the opening portion;
the fusion region including the opening portion disposed on a distal side of a proximal end of the distal side shaft;
a region in which the arc-shaped portion and the proximal side shaft are fused with each other is formed in the fusion region on the proximal side of the opening portion; and
wherein the proximal side shaft and the inner tube shaft are fused with each other over an entire length from the proximal portion to the distal portion of the fusion region.

2. The catheter according to claim 1, wherein a distal position of the fusion region is on a distal side of a proximal position of the distal side shaft and a distal position of the arc-shaped portion of the inner tube shaft and a distal position of the proximal side shaft or on a proximal side of the distal position of the proximal side shaft.

3. The catheter according to claim 1, wherein the inner tube hollow portion in cross section has a circular shape and is configured to receive a guide wire.

4. The catheter according to claim 1, wherein the distal hollow portion in cross section has a semi-circular shape and is configured to receive a dilation fluid.

5. The catheter according to claim 1, further comprising:
a balloon disposed on a distal end side portion of the catheter shaft; and
a hub fixedly attached to a proximal side end portion of the catheter shaft.

6. The catheter according to claim 1, wherein the arc-shaped portion of the inner tube shaft is smaller than a half of the entire circumference of the inner tube shaft in the circumferential direction.

7. The catheter according to claim 1, wherein the proximal side shaft is cut in a slope shape from a distal side toward a proximal side.

8. The catheter according to claim 1, wherein a hollow portion of the distal side shaft and a hollow portion of the proximal side shaft are located so as to be continuous with each other, and wherein a region including a most distal portion of the proximal side shaft is located so as to be adjacent to the inner tube shaft.

9. The catheter according to claim 1, wherein a proximal position of a thermally shrinkable tube is located to be proximal of the arc-shaped portion.

10. The catheter according to claim 1, wherein the proximal side end portion of the distal side shaft has a distal shaft arc-shaped portion in which only a portion in a circumferential direction of an entire circumference extends along the axial direction toward the proximal side.

11. A catheter comprising:
a catheter shaft in which a distal side shaft that has a distal hollow portion;
an inner tube shaft that is disposed inside the distal side shaft, the inner tube shaft having an inner tube hollow portion;
a proximal side shaft having a proximal hollow portion communicating with the distal hollow portion are integrated with each other in a fusion region formed along an axial direction of the proximal side shaft;
the inner tube shaft having an opening portion through which the inner tube hollow portion opens outward, and an arc-shaped portion which extends along the axial direction from the opening portion to a proximal side and which has only a portion of an entire circumference in a circumferential direction of the inner tube shaft, the portion of the entire circumference in the circumference direction of the inner tube shaft being smaller than a half of the entire circumference of the inner tube shaft in the circumferential direction, and wherein the arc-shaped portion is parallel with a center axis of the opening portion; and
wherein the proximal side shaft and the inner tube shaft are fused with each other over an entire length from the proximal portion to the distal portion of the fusion region.

12. The catheter according to claim 11, wherein the fusion region includes the opening portion disposed on a distal side of a proximal end of the distal side shaft.

13. The catheter according to claim 11, further comprising:
a region in which the arc-shaped portion and the proximal side shaft are fused with each other is formed in the fusion region on the proximal side of the opening portion.

14. The catheter according to claim 11, wherein the inner tube hollow portion in cross section has a circular shape and is configured to receive a guide wire, and wherein the distal hollow portion in cross section has a semi-circular shape and is configured to receive a dilation fluid.

15. The catheter according to claim 11, wherein a hollow portion of the distal side shaft and a hollow portion of the proximal side shaft are located so as to be continuous with each other, and wherein a region including a most distal portion of the proximal side shaft is located so as to be adjacent to the inner tube shaft.

16. The catheter according to claim 11, wherein the proximal side end portion of the distal side shaft has a distal shaft arc-shaped portion in which only a portion in a circumferential direction of an entire circumference extends along the axial direction toward the proximal side.

17. A catheter comprising:
- a catheter shaft in which a distal side shaft that has a distal hollow portion, an inner tube shaft that is disposed inside the distal side shaft, and that has an inner tube hollow portion, and a proximal side shaft that has a proximal hollow portion communicating with the distal hollow portion are integrated with each other in a fusion region formed along an axial direction of the proximal side shaft;
- the inner tube shaft having an opening portion through which the inner tube hollow portion opens outward, and an arc-shaped portion which extends from the opening portion to a proximal side and which has only a portion of an entire circumference in a circumferential direction of the inner tube shaft, and wherein the arc-shaped portion is parallel with a center axis of the opening portion;
- the fusion region including the opening portion disposed on a distal side of a proximal end of the distal side shaft;
- a region in which the arc-shaped portion from a distal end of the arc-shaped portion to a proximal end of the arc-shaped portion is fused to the proximal side shaft in the fusion region on the proximal side of the opening portion; and
- wherein the proximal side shaft and the inner tube shaft are fused with each other over an entire length from the proximal portion to the distal portion of the fusion region.

* * * * *